United States Patent [19]

Mahmud et al.

[11] Patent Number: 5,622,557
[45] Date of Patent: Apr. 22, 1997

[54] MINERAL BINDERS COLORED WITH SILICON-CONTAINING CARBON BLACK

[75] Inventors: Khaled Mahmud, Tyngsboro; Jameel Menashi, Lexington; James A. Belmont, Acton; Ralph U. Boes, Concord, all of Mass.

[73] Assignee: Cabot Corporation, Boston, Mass.

[21] Appl. No.: 446,143

[22] Filed: May 22, 1995

[51] Int. Cl.⁶ .................................. C04B 14/36
[52] U.S. Cl. ................ 106/712; 106/475; 106/717; 106/819
[58] Field of Search ............................ 106/712, 717, 106/475, 819

[56]  References Cited

U.S. PATENT DOCUMENTS

| | | | |
|---|---|---|---|
| 1,999,573 | 4/1935 | Odell | 106/425 |
| 2,375,795 | 5/1945 | Krejci | 423/456 |
| 2,564,700 | 8/1951 | Krejci | 423/456 |
| 2,632,713 | 3/1953 | Krejci | 106/475 |
| 2,793,100 | 5/1957 | Welhe | 23/293 R |
| 2,891,595 | 6/1959 | Kuntz et al. | 152/564 |
| 3,094,428 | 6/1963 | Hamilton et al. | 106/472 |
| 3,203,819 | 8/1965 | Steenken et al. | 106/475 |
| 3,317,458 | 5/1967 | Clas et al. | 523/334 |
| 3,390,006 | 6/1968 | Takewell et al. | 106/475 |
| 3,622,650 | 11/1971 | Berstein et al. | 106/475 |
| 3,660,132 | 5/1972 | Illigen et al. | 106/426 |
| 3,663,285 | 5/1972 | Graf et al. | 106/491 |
| 3,689,452 | 9/1972 | Burke, Jr. | 524/96 |
| 3,716,513 | 2/1973 | Burke, Jr. | 523/351 |
| 3,873,489 | 3/1975 | Thurn et al. | 524/262 |
| 3,997,356 | 12/1976 | Thurn et al. | 106/483 |
| 4,006,031 | 2/1977 | Ferch et al. | 106/473 |
| 4,071,496 | 1/1978 | Kraus et al. | 524/495 |
| 4,074,035 | 2/1978 | Powers et al. | 526/185 |
| 4,108,679 | 8/1978 | Szczepanik et al. | 106/475 |
| 4,211,578 | 7/1980 | Scott, IV | 106/475 |
| 4,229,333 | 10/1980 | Wolff et al. | 524/571 |
| 4,297,145 | 10/1981 | Wolff et al. | 106/475 |
| 4,360,627 | 11/1982 | Okado et al. | 524/496 |
| 4,366,139 | 12/1982 | Kühner et al. | 423/449.1 |
| 4,452,638 | 6/1984 | Gallus | 106/669 |
| 4,468,496 | 8/1984 | Takeuchi et al. | 525/233 |
| 4,517,335 | 5/1985 | Wolff et al. | 524/552 |
| 4,537,633 | 8/1985 | Hong | 106/670 |
| 4,590,052 | 5/1986 | Chevallier et al. | 423/335 |
| 4,670,059 | 6/1987 | Hackleman et al. | 106/475 |
| 4,820,751 | 4/1989 | Takeshita et al. | 523/215 |
| 4,822,844 | 4/1989 | Kawakami et al. | 524/496 |
| 4,824,900 | 4/1989 | Sakurai | 524/495 |
| 4,866,131 | 9/1989 | Fujimaki et al. | 525/96 |
| 4,894,420 | 1/1990 | Scriver | 525/237 |
| 5,008,223 | 4/1991 | Speer et al. | 106/450 |
| 5,149,732 | 9/1992 | Igarashi et al. | 524/315 |
| 5,159,009 | 10/1992 | Wolff et al. | 106/475 |
| 5,162,409 | 11/1992 | Mroczkowski | 524/262 |
| 5,227,425 | 7/1993 | Rauline | 524/493 |
| 5,281,261 | 1/1994 | Lin | 106/20 R |
| 5,286,291 | 2/1994 | Bernhardt et al. | 106/475 |
| 5,294,253 | 3/1994 | Carlson et al. | 106/475 |
| 5,328,949 | 7/1994 | Sandstrom | 524/262 |
| 5,336,730 | 8/1994 | Sandstrom | 525/332.6 |
| 5,401,789 | 3/1995 | Wolf et al. | 524/188 |
| 5,430,087 | 7/1995 | Carlson et al. | 106/475 |

FOREIGN PATENT DOCUMENTS

| | | |
|---|---|---|
| 0050354A1 | 4/1982 | European Pat. Off. . |
| 0411160A1 | 2/1991 | European Pat. Off. . |
| 0501227A1 | 9/1992 | European Pat. Off. . |
| 0641823A1 | 3/1995 | European Pat. Off. . |
| 0646621A1 | 4/1995 | European Pat. Off. . |
| 0711805A1 | 5/1996 | European Pat. Off. . |
| 3502494A1 | 8/1985 | Germany . |
| 5-178604 | 7/1993 | Japan . |
| 7-30269 | 4/1995 | Japan . |
| 1139620 | 1/1969 | United Kingdom ............ 106/475 |
| 1363429 | 8/1974 | United Kingdom ............ 106/717 |
| 1363428 | 8/1974 | United Kingdom ............ 106/717 |
| 2044741 | 10/1980 | United Kingdom ............ 106/475 |
| WO92/13983 | 8/1992 | WIPO . |

OTHER PUBLICATIONS

PCT International Search Report for Application No. PCT/US96/07312 (Sep. 1996).
PCT International Search Report for Application No. PCT/US96/07309 (Sep. 1996).
WPI/Derwent 93-261471-Abstract of Japanese Patent No. 5178604 (Jul. 20, 1993).
Patent Abstracts of Japan, Publication No. JP6067421, Mar. 11, 1994.
Derwent Abstract, Japanese Patent Application No. 80-73657, Mar. 19, 1996.
Derwent Abstract, WPI Acc No. 78-73373A/41, Japanese Patent Application No. 53-100190, (Sep. 1978).
Derwent Abstract, WPI Acc No. 95-019436/03, Japanese Patent Application No. 63-06289, (Nov. 1994).
Derwent Abstract, WPI Acc No. 92-369382/45, Japanese Patent Application No. 4-270199, (Sep. 1992).
Derwent Abstract, WPI Acc No. 90-335599/45, DD No. 279537, (Jun. 1990).
Derwent Abstract, WPI Acc No. 90-128540/17, Japanese Patent Application No. 2-077483, (Mar. 1990).

(List continued on next page.)

Primary Examiner—Anthony Green

[57] ABSTRACT

Binder compositions are provided which include a mineral binder and a silicon-containing carbon black. The silicon-containing carbon black can have attached an ionic or ionizable organic group or can be oxidized. Silicon-containing carbon blacks may be prepared by a furnace method. The binder compositions of the present invention have improved coloring and weathering properties in comparison to binder compositions prepared with conventional carbon blacks. Furthermore, the binder compositions that incorporate silicon-containing carbon blacks having ionic or ionizable organic groups attached exhibit excellent dispersibility, even in pelletized form. Articles such as roofing tiles can be prepared from the binder compositions. Also contemplated is a method of improving the color stability of a mineral binder composition. Silicon-containing carbon blacks as described above are added to the mineral binder composition.

38 Claims, 1 Drawing Sheet

OTHER PUBLICATIONS

Derwent Abstract, WPI Acc No. 88–261546/37, Japanese Patent Application No. 63–190800, (Aug. 1988).

Derwent Abstract, WPI Acc No. 88–052867/08, Japanese Patent Application No. 63–008442, (Jan. 1988).

Derwent Abstract, WPI Acc No. 87–034097/05, Japanese Patent Application No. 61–291659, (Dec. 1986).

Derwent Abstract, WPI Acc No. 86–037092/06, U.S. Patent No. 4,605,542, (Aug. 1986).

Dialog Abstract No. 1933022, U.S. Patent 4,820,751, (Apr. 1989).

Chemical Abstract vol. 114, No. 14, No. 124715d (Sep. 1990).

Chemical Abstract vol. 112, No. 18, No. 160248w, (Aug. 1989).

Chemical Abstract vol. 110, No. 6, No. 48370n, (Jul. 1988).

Chemical Abstract vol. 69, No. 18, No. 68396p, (Oct. 1967).

Chemical Abstract vol. 94, No. 16, No. 122906m, (Dec. 1980).

Chemical Abstract vol. 66, No. 24, No. 105491b, (Dec. 1966).

Chemical Abstract vol. 67, No. 2, No. 3806m, (Nov. 1966).

Chemical Abstract vol. 102, No. 4, No. 28447z, (Aug. 1984).

Chemical Abstract vol. 100, No. 22, No. 176125s, (Dec. 1983).

Chemical Abstract vol. 106, No. 28, No. 224473b, (Nov. 1987).

Chemical Abstract vol. 94, No. 8, No. 48630y, (Sep. 1980).

Chemical Abstract vol. 88, No. 22, No. 161466p, (Feb. 1978).

Chemical Abstract vol. 104, No. 12, No. 90590k, (Aug. 1985).

Chemical Abstract vol. 105, No. 8, No. 61488y, (Dec. 1985).

Ouyang et al., "Carbon Black Effects on Treadwater," Presented at a Meeting of the Rubber Division, American Chemical Society, Las Vegas, Nevada, May 29–Jun. 1, 1990.

Agostini, et al., "New Compound Technology," Goodyear Technical Center Luxembourg (No Date).

Dialog Abstract of Japanese Application No. 4–362009, 1992 (Dec. 1992).

Dialog Abstract of Japanese Application No. 4–276000, 1992 (Oct. 1992).

Studebaker et al., "The Rubber Compound and its Composition," *Science and Technology of Rubber*, Academic Press, 1978, Chapter 9, pp. 367–375 No Month.

"Tires," Reprinted from *Encyclopedia of Polymer Science and Engineering*, vol. 16, Second Edition, 1969, pp. 834–861 No Month.

Concise Encyclopedia of Polymer Science and Engineering, Wiley, 1990, pp. 104–105 No Month.

Carbon (Carbon Black) reprinted from Kirk–Othmer: Encyclopedia of Chemical Technology, vol. 4, Third Edition, pp. 631–643, 1978 No Month.

Priority Document (U.S. Patent Application Serial No. 08/079,191) for European Patent Application No. EP 0 632 094 A1 (Jun. 1993).

MINERAL BINDERS COLORED WITH SILICON-CONTAINING CARBON BLACK

RELATED APPLICATIONS

This application is related to the following U.S. patent applications identified by title and serial number, filed on even date herewith: Elastomeric Compounds Incorporating Silicon-Treated Carbon Blacks (Ser. No. 08/446,141); Elastomeric Compounds Incorporating Partially Coated Carbon Blacks (Ser. No. 08/446,140); and Elastomeric Compounds Incorporating Silicon-Treated Carbon Blacks and Coupling Agents (Ser. No. 08/446,142).

FIELD OF THE INVENTION

This invention relates to mineral binder systems which include silicon-containing carbon black products as colorants.

BACKGROUND OF THE INVENTION

Mineral binders such as concrete, cement, mortar, and exterior plaster are often colored to enhance their aesthetic appeal. Coloring can be accomplished either by applying a colored coating to exposed surfaces of a cured or set mineral binder or by premixing small amounts of one or more pigments in a mineral binder system prior to setting to color the system uniformly. The pigment(s) in the premix method can be added either to a dry mineral mix, as for example, in the case of concrete, to the cement-sand mixture, or can be added to water used to set the mineral mix. The premixing method of coloring is preferred because colored surface coatings are not permanent but peel, fade, and hence weather more rapidly than premixed colorants.

Pigments for mineral binder systems which are exposed to outdoor conditions must be alkali-resistant, lightfast, resistant to industrial atmospheres, and must weather at a rate comparable to the rate at which the binder itself weathers so that surface appearance does not change unevenly over time. Additionally for ease of handling, the pigment should be relatively dust-free to facilitate mixing to achieve maximum coloring power and should be easily dispersible.

Black pigments are particularly desirable colorants for mineral binder systems because a large variety of colors and color shades can be obtained by their use either alone or in combination with other pigments. Black iron oxides and carbon blacks are common black pigments.

Carbon blacks exhibit excellent coloring properties, alkali-resistance, lightfastness, and chemical stability. However, carbon blacks are not preferred pigments in mineral binder systems exposed to outdoor weathering because the surface appearance of bodies containing carbon black exhibit undesirable changes such as fading with weathering. Fading is attributed to a preferential leaching out and washing away of the carbon black pigment from the mineral binder system. Furthermore, when carbon black is used in combination with other colorants, the appearance of the other colorant becomes more pronounced with weathering over time due to the selective leaching out and washing away of carbon black pigment. Consequently, carbon black has had limited use in systems which are exposed to outdoor weathering.

Another drawback to the use of carbon black as a colorant in indoor or outdoor applications is that, depending on the physical form in which it is supplied, carbon blacks are either excessively dusty or difficult to disperse. The process used for incorporating carbon blacks into binder systems depends on the form in which the pigment is supplied and on the processing equipment available to the user. Powdery carbon blacks have bulk densities ranging from about 0.02 to 0.1 g/cc and are termed "fluffy" blacks. Because of their low densities and large surface areas, the fluffy products are cohesive, have very poor conveying properties, are difficult to handle in bulk, and are usually supplied in bagged form. However, fluffy carbon blacks are dispersible and can develop full coloring potential by relatively simple grinding procedures.

Handling properties for a given grade of carbon black improve with increased densification such as by pelletization. For example, fluffy blacks are typically densified by pelletizing to improve bulk handling properties. Such procedures provide bulk densities ranging from about 0.2 to 0.7 g/cc. However, dispersibility is progressively degraded as the pellet density increases. Thus, there is a tradeoff between improvement in bulk handling properties and degradation in dispersibility. Because of the advantages of increased cleanliness, pelletized carbon blacks are generally preferred for introducing carbon blacks into mineral binder systems despite the need for increased grinding or milling to form a uniform, intimate mix.

Carbon black agglomerates, whether in pelletized or fluffy form, must be broken down primarily to aggregates (smallest dispersible units of carbon black) for full color development. This is accomplished either by milling the dry mix or by predispersing the carbon black in the aqueous medium. For example, in the preparation of colored concrete, carbon black can be milled into a dry sand-cement mixture, and subsequently, the requisite amount of water necessary for setting the mix can be added. Alternatively, an aqueous dispersion of the carbon black, in all or part of the requisite volume of water necessary for setting the mix, can be uniformly blended into the sand-cement mixture.

Since carbon blacks tend to be hydrophobic, surface active agents are often used to promote wetting, to enhance the dispersion process, and to aid dispersion stabilization. For example, U.S. Pat. No. 4,006,031 discloses the use of fluorine-containing wetting agents used with carbon blacks in an attempt to improve the weathering properties of mineral binder systems. European Patent Publication No. 50354 describes the use of surface-active polymers which disperse the carbon black in an aqueous medium used to set the mineral binder system. The polymer becomes inactive after drying. However, in dry milling or predispersion, the carbon black, whether in fluffy or pelletized form, must still be milled to attain satisfactory pigment dispersion.

Thus, there remains a need for carbon black colorants for mineral binder systems which exhibit both improved weatherability properties and/or are easily dispersed in pelletized form.

SUMMARY OF THE INVENTION

Figure 1:
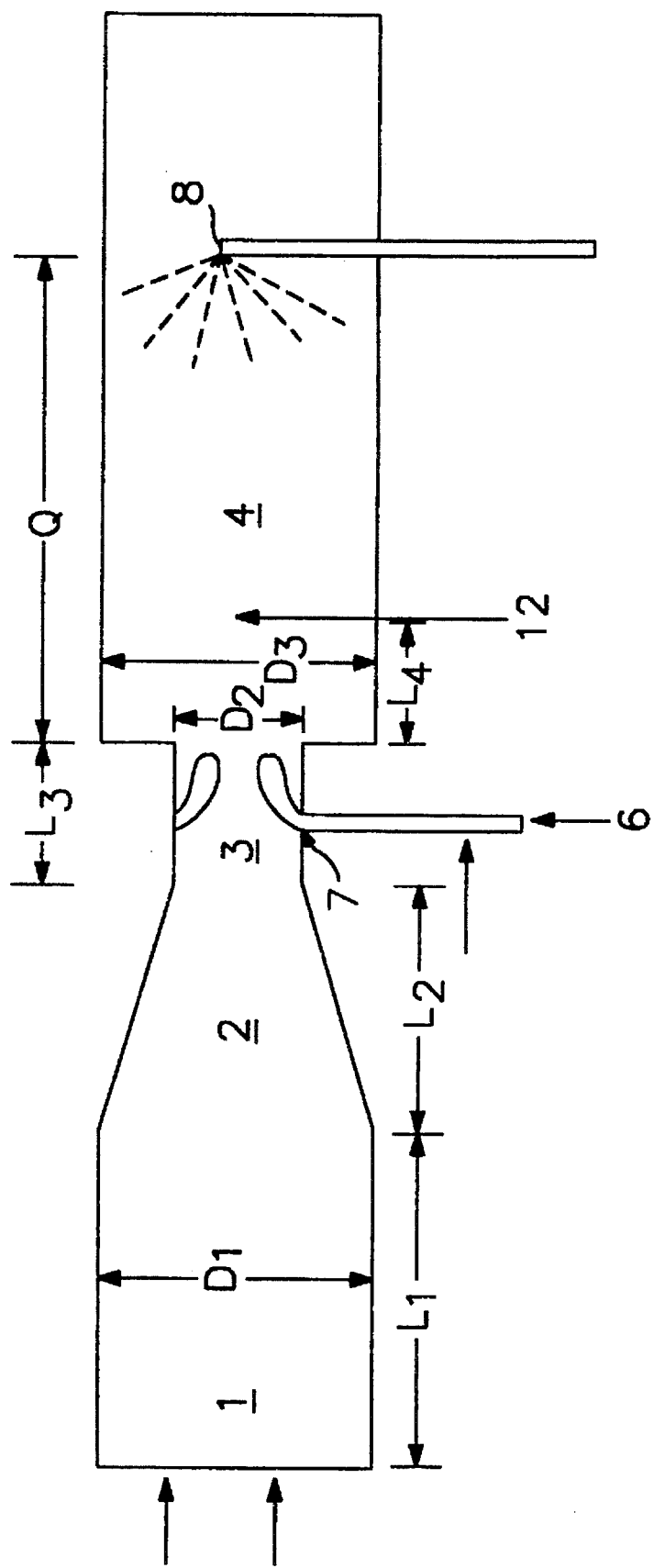
FIG. 1 is a schematic view of a portion of one type of furnace carbon black reactor which may be used to produce silicon-containing carbon blacks.

Binder compositions are provided which comprise a mineral binder and silicon-containing carbon black. The silicon-containing carbon black can have attached an ionic or ionizable organic group or can be oxidized. The silicon containing carbon blacks may be prepared by a furnace method. The binder compositions of the present invention have improved coloring and weathering properties in comparison to binder compositions prepared with conventional carbon blacks. Furthermore, the binder compositions that incorporate silicon-containing carbon blacks having ionic or ionizable organic groups attached exhibit excellent dispersibility, even in pelletized form. Articles such as roofing tiles can be prepared from the binder compositions of the present invention.

Also contemplated is a method of improving the color stability of a mineral binder composition. Silicon-containing carbon blacks as described above are added to the mineral binder composition.

DETAILED DESCRIPTION OF THE INVENTION

The present inventors have discovered that the weathering properties of carbon black pigmented mineral binder compositions and articles can be improved by the incorporation of silicon-containing carbon black(s) therein.

Mineral binders include, but are not limited to, concrete, cement, mortar, exterior plaster formulations, and the like. Conventionally known additives for mineral binder systems may also be incorporated in the mineral binder or in the binder composition.

Carbon blacks generally exist in the form of aggregates. The silicon-containing carbon blacks of the present invention are typically in aggregate form and are not physical mixtures or blends of silicon-containing aggregates or particles and carbon black aggregates. The aggregates of the present invention generally include a major portion of carbon and a minor portion of silicon. The silicon-containing carbon black aggregates of the present invention include at least one silicon-containing region at at least one portion of the surface of the carbon black aggregate.

The morphology of silicon-containing carbon blacks can be observed, for example, by scanning transmission electron microscopy (STEM). When STEM is coupled with energy dispersive x-ray (EDX) analysis, the components or elemental compositions of the individual silicon-containing carbon black aggregates can be identified. A physical mixture of carbon black and silica will result in the identification of aggregates which show mostly Si content and little carbon content. Thus, when multiple aggregates are examined in a mixture, some of the aggregates will show a high Si/C signal ratio, corresponding to particles or aggregates of silica.

In a typical analysis, for example, five mg of carbon black can be dispersed into 20 ml of chloroform and subjected to ultrasonic energy using a probe sonicator (W-385 Heat Systems Ultra Sonicator). A 2 ml aliquot would then be dispersed into 15 ml of chloroform using a probe sonicator for three minutes. The resulting dispersion is placed on a 200 mesh, nickel grid with aluminium substrate. The grid is then placed under a Fisons HB501 Scanning Transmission Electron Microscope (Fisons, West Sussex, England) equipped with an Oxford Link AN10000 Energy Dispersive X-ray Analyzer (Oxford Line, Concord Mass.).

Initially the grid is scanned for potential silica aggregates at low magnification (less than 200,000×). This is done by searching for aggregates that have the highest Si/C count ratio. After this initial scan, typically thirty aggregates are selected for detailed analysis at higher magnification (from between 200,000× and 2,000,000×). The selected aggregates should include all of the aggregates which contain the highest Si/C count ratios as identified by the initial scan. The highest ratios of Si/C counts are thus determined. For example, a mixture of N-234 carbon black and 3.7% by weight of silica (L90) (1.7% Si) has a highest Si/C count ratio per aggregate of 49. A silicon-containing carbon black prepared, as further described below, by injecting octamethylcyclotetrasiloxane into the feedstock (3.28% Si) has a maximum Si/C count ratio of 0.27. Thus, a low Si/C count ratio is indicative of a silicon-containing carbon black.

The presence of silicon-containing regions at the surface can be determined, for example, by treatment of the silicon-containing carbon blacks with a hydrofluoric acid solution, for example, 10 volume %, which will dissolve at least a portion of the silicon in silicon-containing regions at at least one portion of the surface of the carbon black aggregate. For example, hydrofluoric acid (HF) extraction can be performed by taking 5 gms of the carbon black and then extracting it with 100 ml of 10 percent v/v of the acid for 1 hour.

Silicon-containing carbon blacks of the present invention include, but are not limited to, carbon black aggregates in which the silicon is distributed throughout the carbon black or a portion thereof but at least a portion of the silicon containing regions are accessible to the surface of the carbon black aggregate. For example, the carbon black may form a matrix through at least a portion of which the silicon is distributed.

These silicon-containing carbon blacks are carbon blacks that are typically obtained by introducing a volatilizable silicon-containing compound into a carbon black reactor during the manufacture of the carbon black, and may be produced, for example, in a modular or "staged," furnace carbon black reactor method as depicted in FIG. 1.

The furnace carbon black reactor of FIG. 1 has a combustion zone 1, with a zone of converging diameter 2; a feedstock injection zone with restricted diameter 3; and a reaction zone 4.

To produce carbon blacks with the reactor described above, hot combustion gases are generated in combustion zone 1 by contacting a liquid or gaseous fuel with a suitable oxidant stream such as air, oxygen, or mixtures of air and oxygen. Among the fuels suitable for use in contacting the oxidant stream in combustion zone 1 to generate the hot combustion gases, are included any readily combustible gas, vapor, or liquid streams such as natural gas, hydrogen, methane, acetylene, alcohols, or kerosene. It is generally preferred, however, to use fuels having a high content of carbon-containing components and, in particular, to use hydrocarbons. The ratio of air to fuel varies with the type of fuel utilized. When natural gas is used to produce silicon-containing carbon blacks, the ratio of air to fuel may be from about 10:1 to about 1000:1. To facilitate the generation of hot combustion gases, the oxidant stream may be pre-heated.

The hot combustion gas stream flows downstream from zones 1 and 2 into zones 3 and 4. The direction of the flow of hot combustion gases is shown in FIG. 1 by the arrow. Carbon black feedstock 6 is introduced at point 7 into the feedstock injection zone 3. The feedstock is injected into the gas stream through nozzles designed for optimal distribution of the oil in the gas stream. Such nozzles may be either single or bi-fluid. Bi-fluid nozzles may use steam or air to atomize the fuel. Single-fluid nozzles may be pressure atomized or the feedstock may be directly injected into the gas stream. In the latter instance, atomization occurs by the force of the gas stream.

Carbon blacks can be produced by the pyrolysis or partial combustion of any liquid or gaseous hydrocarbon. Preferred carbon black feedstocks include petroleum refinery sources such as decanted oils from catalytic cracking operations, as well as the by-products from coking operations and olefin manufacturing operations.

The mixture of carbon black-yielding feedstock and hot combustion gases flows downstream through zone 3 and 4. In the reaction zone portion of the reactor, the feedstock is pyrolyzed to carbon black. The reaction is arrested in the quench zone of the reactor. Quench 8 is located downstream of the reaction zone and sprays a quenching fluid, generally water, into the stream of newly formed carbon black particles. The quench serves to cool the carbon black particles, to reduce the temperature of the gaseous stream, and to decrease the reaction rate. Q is the distance from the beginning of reaction zone 4 to quench point 8, and will vary according to the position of the quench. Optionally, quenching may be staged or may take place at several points in the reactor.

After the carbon black is quenched, the cooled gases and carbon black pass downstream into any conventional cooling and separating means whereby the carbon black is recovered. The separation of the carbon black from the gas stream is readily accomplished by conventional means such as a precipitator, cyclone separator, bag filter, or other means known to those skilled in the art. After the carbon black has been separated from the gas stream, it is optionally subjected to a pelletization step.

These silicon-containing carbon blacks are made by introducing a volatilizable silicon compound into the carbon black reactor at a point upstream of the quench zone. Useful volatilizable silicon compounds are those which are volatizable at carbon black reactor temperatures. Suitable volatilizable silicon compounds include, but are not limited to, silicates such as, for example, tetramethoxy- and tetraethoxy-orthosilicate (TEOS); silanes such as, for example, tetrachlorosilane and trichloromethylsilane; volatile silicone polymers such as octamethylcyclotetrasiloxane (OMTS); and mixtures of any of the foregoing.

The volatilizable silicon compound may be premixed with the carbon black-forming feedstock and introduced with the feedstock into the reaction zone. Alternatively, the silicon compound may be introduced to the reaction zone separately from the feedstock injection point. Such introduction may be upstream or downstream from the feedstock injection point, provided the silicon compound is introduced upstream from the quench zone. For example, referring to FIG. 1, the silicon compound may be introduced at point 12, or any other point in the reaction zone. Upon volatilization and exposure to high temperatures in the reactor, the silicon compound is decomposed and reacts with other species in the reaction zone, yielding silicon-containing carbon black.

If the silicon precursor is introduced substantially simultaneously with the feedstock, a silicon-containing carbon black compound is obtained wherein the silicon-containing regions are distributed through the aggregate.

In a second embodiment of the furnace reactor method, the silicon compound is introduced to the reaction zone at a point where the carbon black formation process has commenced, but the reaction stream has not yet been subjected to the quench. In this embodiment, silicon-containing carbon blacks are obtained in which the silicon, or a silicon-containing species is present primarily at or near the surface of the carbon black The present inventors also believe that the silicon-containing carbon blacks of the present invention can include, but are not limited to, carbon black aggregates that are coated so that at least a portion of the carbon black remains uncoated and the carbon black is not completely encapsulated. The coating may form a partial shell around the carbon black but in this form, typically does not permeate the carbon black matrix other than to any degree necessary for adherence or adsorption of the shell to the carbon black core.

While the present inventors have not been able to duplicate such carbon blacks, it is believed that such silicon-containing carbon blacks may be prepared, for example, by precipitation methods known in the art such as, for example, the method described in Japanese (Kokai) Patent Application No. HEI 5(1993)-178604. A silicon-containing reactant, for example an organo-silicate such as tetraethyl orthosilicate or a silane such as tetraethoxysilane, is diluted with a solvent such as methanol to produce a silicon compound solution with a concentration of about 1 to about 20% by weight of the silicon compound. Another solution is made by adding about 5 to about 20% of about a 28% aqueous ammonia solution to ethanol.

Carbon black is added to the ammonia solution, while continuously stirring the mixture. Simultaneously, the silicon compound solution is added dropwise. After up to several hours of this operation, the material is filtered and dried. The obtained product is carbon black at least partially coated with silica.

Preferably, the added silicon comprises from about 0.1 to about 20 parts by weight and most preferably from about 1 to about 10 parts by weight based upon 100 parts by weight of the silicon-containing carbon black.

The silicon-containing carbon blacks useful in the present invention may be oxidized by oxidizing agents such as nitric acid and the like.

Furthermore, these silicon-containing carbon blacks may be modified by attaching an organic group that includes an ionic or ionizable group. These modified silicon-containing carbon blacks may be prepared by reacting a silicon-containing carbon black with a diazonium salt in a liquid reaction medium to attach at least one organic group to the surface of the carbon black. The diazonium salt may contain the organic group to be attached to the carbon black. A diazonium salt is an organic compound having one or more diazonium groups. Preferred reaction media include water, any medium containing water, and any medium containing alcohol. Water is the most preferred medium. Various methods of preparation are described in a U.S. Ser. No. 08/356,660, filed Dec. 15, 1994.

A diazonium salt used in the preparation of modified silicon-containing carbon blacks need only be sufficiently stable to allow reaction with the carbon black. Thus, the reaction can be carried out with some diazonium salts otherwise considered to be unstable and subject to decomposition. Some decomposition processes may compete with the reaction between the silicon-containing carbon black and the diazonium salt and may reduce the total number of organic groups attached to its surface. Further, the reaction may be carried out at elevated temperatures where many diazonium salts may be susceptible to decomposition. Elevated temperatures may also advantageously increase the solubility of the diazonium salt in the reaction medium and improve its handling during the process. However, elevated temperatures may result in some loss of the diazonium salt due to other decomposition processes.

The silicon-containing carbon black can be reacted with a diazonium salt either as a dilute, easily stirred, aqueous slurry, or preferably in the presence of the proper amount of water for silicon-containing carbon black pelletization. The diazonium salt may either be generated in the presence of the silicon-containing carbon black, or it may be generated separately from the silicon-containing carbon black.

Organic groups which may be attached, preferably chemically, to the silicon-containing carbon black preferably are organic groups substituted with an ionic or an ionizable group as a functional group. An ionizable group is one which is capable of forming an ionic group in the medium of use, i.e., the binder composition. The ionic group may be anionic or cationic, and the ionizable group may form an anion or a cation.

Ionizable functional groups that form anions include, but are not limited to, acidic groups or salts of acidic groups, including those derived from organic acids. Preferably the organic group has (a) an aromatic group or a $C_1$-$C_{12}$ alkyl group and (b) at least one acidic group having a pKa of less than 11, or a mixture of at least one acidic group having a pKa of less than 11. The pKa of the acidic group refers to the pKa of the organic group as a whole, not just the acidic substituent. More preferably, the pKa is less than 10, and most preferably, the pKa is less than 9. The aromatic group may be unsubstituted or substituted, with, for example, one or more alkyl group. Preferably, the aromatic group or alkyl group of the organic group is directly attached to the silicon-containing carbon black. The $C_1$-$C_{12}$ alkyl group may be branched or unbranched and is preferably ethyl. Most preferably, the organic group is a phenyl or a naphthyl group, and the acidic group is a sulfonic acid group, a sulfinic acid group, a phosphonic acid group, or a carboxylic acid group. Preferred acidic groups include, but are not limited to, —COOH, —$SO_3H$ and —$PO_3H_2$ and their salts, such as, for example, —COONa, —COOK, —COO$^-$NR$^+_4$, —$SO_3$Na, —HPO$_3$Na, —SO3$^-$NR$^+_4$ and —PO$_3$Na$_2$, where R is an alkyl or phenyl group. Particularly preferred ionizable substituents are —COOH and —$SO_3H$ and their sodium and potassium salts.

Most preferably, the organic group is a substituted or unsubstituted sulfophenyl group or a salt thereof; or a substituted or unsubstituted (polysulfo) phenyl group or a salt thereof; or a substituted or unsubstituted sulfonaphthyl group or a salt thereof. A preferred substituted sulfophenyl group is hydroxysulfophenyl group or a salt thereof. Specific organic groups having an ionizable functional group forming an anion are p-sulfophenyl, 4-hydroxy-3-sulfophenyl, and 2-sulfoethyl.

Quaternary ammonium groups (—NR$_3^+$) and quaternary phosphonium groups (—PR$_3^+$) are non-limiting examples of cationic groups that can be attached to the organic groups as discussed above. Preferably, the organic group includes an aromatic group such as a phenyl or a naphthyl group and a quaternary ammonium or a quaternary phosphonium group. The aromatic group is preferably directly attached to the silicon-containing carbon black. Quaternary cyclic amines and quaternary aromatic amines can also be used as the organic group. Thus, N-substituted pyridinium compounds, such as N-methyl-pyridyl, can be used in this regard.

An advantage of the silicon-containing carbon black products having an attached organic group substituted with an ionic or an ionizable group is that these modified silicon-containing carbon black products may have increased water dispersibility relative to the corresponding unmodified silicon-containing carbon blacks. In general, water dispersibility of a silicon-containing carbon black product increases with the number of organic groups attached to the silicon-containing carbon black having an ionizable group or the number of ionizable groups attached to a given organic group. Thus, increasing the number of ionizable groups associated with the silicon-containing carbon black products should increase their water dispersibility. Accordingly, water dispersibility can be controlled and optimized.

When water dispersible modified silicon-containing carbon blacks are prepared, it is preferred to ionize the ionic or ionizable groups in the reaction medium. The resulting product may be used as is or diluted prior to use. The modified silicon-containing carbon black may be pelletized, preferably by a conventional wet process, pin pelletizing operation.

The modified silicon-containing black products may be dried by techniques used for conventional carbon blacks including, but are not limited to, drying in ovens and rotary kilns. Overdrying, however, may cause a loss in the degree of water dispersibility. If a modified silicon-containing carbon black does not disperse in an aqueous vehicle as readily as desired, the modified silicon-containing carbon black may be dispersed using conventionally known techniques such as milling or grinding.

Modified and unmodified silicon-containing carbon blacks may be incorporated in the binder compositions of the present invention either in solid form or as a preformed liquid dispersion. Preferably, modified or unmodified silicon-containing carbon black is present in an amount less than or equal to 5 parts by weight and most preferably from about 0.1 to about 1 part by weight based upon 100 parts by weight of total binder composition.

The binder compositions are prepared by combining the silicon-containing carbon black and the mineral binder by methods conventional in the art such as, for example, mixing, preferably by a low shear method. The silicon-modified carbon black can be mixed with a dry mineral binder or can be premixed with a setting liquid such as, for example, water, and then added to the mineral binder.

Articles may be prepared from the binder compositions of the present invention by methods known to those skilled in the art. Examples of such articles include, but are not limited to, roofing tiles and building faces.

DESCRIPTION OF THE PREFERRED EMBODIMENTS

The following examples illustrate the invention without limitation. All parts are given by weight unless otherwise indicated.

Analytical Methods

The structure level of the carbon blacks and silicon-containing carbon blacks were determined using n-dibutyl phthalate absorption (DBP) (ASTM test procedure D 2414-93) and crushed DBP (ASTM test procedure D 3493-86). Surface area was determined by nitrogen adsorption (ASTM test procedure D 3037-Method A). The silicon content of the samples were determined by ashing (ASTM test procedure D 1506-94). Ash values were used to compute the percent Si in the samples. Tint strength was determined by ASTM test procedure D 3265-93.

Pin pelletizing was accomplished using a pilot scale continuous pin pelletizer. The unit included a 25.5-cm (10-inch) diameter by 91-cm (36-inch) long cylindrical body with a rotor running along its axis. The rotor, fitted with about seventy 1.27-cm (0.5-inch) diameter pins extending almost to the walls of the unit, was rotated at 1000 RPM to form pellets. Water was used as the cohesive fluid in the pellet formation process.

Product dispersibility was measured by dispersing the various products in an aqueous medium having a pH of about 10 under low shear conditions with a magnetic stirrer for 30 minutes. Cetyl trimethyl ammonium bromide surfactant was added to the medium of unmodified non-silicon-containing carbon blacks. Slurry optical density, $(OD)_{low\ shear}$, was determined at a wavelength of 550 nm. The slurry was then sonified (to reflect intense milling), and the slurry optical density, $(OD)_{sonified}$, was determined. The percent change in optical density before and after sonification was calculated.

$$\Delta(OD)=100[(OD)_{sonified}-(OD)_{low\ shear}]/(OD)_{sonified}$$

A large percent change in this value indicates poor low shear dispersibility for the dispersion conditions employed.

Reflectance values from reflectance spectra of unweathered and weathered concrete forms were used to compute the International Commission on Illumination CIE 1976 L*, a*, and b* values. L* represents the lightness coordinate running from 0 for a pure black to 100 for a pure white; a* represents the red-green coordinate with its value becoming larger as the degree of redness increases; b* represents the yellow-blue coordinate with its value becoming larger as the degree of yellowness increases.

Concrete forms were weathered by contacting the concrete forms for 30 seconds with undiluted SURE CLEAN®600 detergent (a blend of organic and inorganic acids combined with wetting agents which is normally diluted with water and employed to clean new masonry—ProSoco -Inc., Kansas City, Kans.). The concrete forms were washed with copious amounts of distilled water and were dried. The surface reflectances were again determined. The neat, undiluted detergent vigorously attacks the alkaline concrete so that some of the surface layers are washed away. Changes in L*, a*, and b*, i.e., $\Delta L^*$, $\Delta a^*$ and $\Delta b^*$, before and after treatment were used to measure preferential leaching. Thus, the change in color on washing, given by the difference in the L*, a* and b* values before washing subtracted from the same values found after washing give the $\Delta L^*$, $\Delta a^*$ and $\Delta b^*$ values.

$\Delta L^*$=L*(after washing)–L*(before washing), $\Delta a^*$=a*(after washing)–a*(before washing), and $\Delta b^*$=b*(after washing)–b*(before washing).

Preparation of ASTM N-234 Carbon Black

ASTM N-234 carbon black was prepared using a pilot scale reactor generally as depicted in FIG. 1 and having the following dimensions.

TABLE A

| Reactor Dimensions | |
| --- | --- |
| $D_1$ | 4 inches |
| $D_2$ | 2 inches |
| $D_3$ | 5 inches |
| $L_1$ | 4 inches |
| $L_2$ | 5 inches |
| $L_3$ | 7 inches |
| $L_4$ | 1 foot |
| Q | 4.5 feet |

The reaction conditions set forth in Table B below were employed. A structure control additive (potassium acetate solution) was injected into the feedstock to maintain the specification structure of the N-234 carbon black.

A commercially available example of N-234 is Vulcan®7H carbon black from Cabot Corporation, Boston, Mass.

TABLE B

| Reactor Conditions | |
| --- | --- |
| Conditions | Carbon Black N-234 |
| Air Rate, kscfh | 12.8 |
| Gas Rate, kscfh | 0.94 |
| feedstock rate, lbs/hr | 166 |
| Si compound rate, lbs/hr | 0 |

EXAMPLE 1

Preparation of Silicon-Containing Carbon Blacks

A pilot scale reactor as described above and as illustrated in FIG. 1, was used to produce silicon-containing carbon black by injecting a silicon compound into a hydrocarbon feedstock under the process conditions listed in Table 1 below. Since changes in reaction temperature are known to alter the surface area of the black, and reaction temperature is very sensitive to the total flowrate of the feedstock in the injection zone (Zone 3, FIG. 1) the feedstock flowrate is adjusted downward to compensate approximately for the introduction of the silicon compound, such that a constant temperature is maintained. A structure control additive (potassium acetate solution) was injected into the feedstock at a flowrate consistent for the preparation of ASTM N-234 carbon black. The flowrate of this additive was maintained constant throughout the preparation of the silicon-containing carbon black.

TABLE 1

| Process Conditions | |
| --- | --- |
| Air Rate, kscfh | 12.8 |
| Gas Rate, kscfh | 0.94 |
| Oil Rate, lbs/hr | 155 |
| OMTS Rate, lbs/hr | 4 |

The resultant silicon-containing carbon black was analyzed for silicon content and surface area. Results are listed in Table 2 below.

TABLE 2

| Silicon-Containing Carbon Black Properties | |
| --- | --- |
| % Silicon in Carbon black | 1.6 |
| DBP, cc/100 g | 115 |
| CDBP, cc/100 g | 102.2 |
| t-Area, m²/g | 119.3 |
| $N_2$ area, m²/g | 129.2 |

EXAMPLE 2

Preparation of Silicon-Containing Carbon Black

Silicon-containing carbon black was prepared by injecting a silicon compound after the plane of oil injection at point 12, as indicated in FIG. 1. Process conditions are listed in Table 3 below.

TABLE 3

| Process Conditions | |
|---|---|
| Air Rate, kscfh | 12.8 |
| Gas Rate, kscfh | 0.94 |
| Oil Rate, lbs/hr | 160 |
| TEOS Rate, lbs/hr | 17.6 |

The resultant silicon-containing carbon black was analyzed for silicon content and surface area. Results are illustrated in Table 4 below.

TABLE 4

| Silicon-Containing Carbon Black Properties | |
|---|---|
| % Silicon in Carbon black | 2.3 |
| DBP, cc/100 g | 131 |
| CDBP, cc/100 g | 114.3 |
| $N_2$ area, $m^2/g$ | 127 |

EXAMPLES 3–7

Silicon-Containing Carbon Blacks Produced Via Addition of a Silicon Compound to the Feedstock A series of silicon-containing carbon blacks were produced by addition of either tetraethoxy orthosilicate (TEOS) or octamethyl cyclotetrasiloxane (OMTS) to a feedstock used to form carbon black. The resultant products were then continuously pelletized. The furnace conditions were adjusted to form products having similar surface areas as illustrated in Example 1. The silicon compound employed, the percent by weight of silicon in the carbon black, the DBP, the surface areas, and the tint strengths of the silicon-containing carbon blacks formed are listed in Table 5 below.

TABLE 5

Characteristics of the Silicon-Containing Carbon Blacks Formed by Addition of a Volatile Silicon Compound To the Feedstock

| Example Number | Silicon Compound | Weight % Silicon | DBP cc/100 g | $N_2$ Area $m^2/g$ | Tint Strength |
|---|---|---|---|---|---|
| 3 | OMTS | 1.5 | 115 | 129 | 121 |
| 4 | OMTS | 2.4 | 122 | 139 | 121 |
| 5 | OMTS | 3.4 | 109 | 135 | 124 |
| 6 | TEOS | 3.5 | 107 | 136 | 113 |
| 7 | OMTS | 5.2 | 105 | 151 | 109 |

EXAMPLES 8–11

Silicon-Containing Carbon Blacks Produced Via Addition of a Silicon Compound to the Furnace After Commencement of Formation of Carbon Black Silicon-containing carbon blacks were produced by the addition of tetraethoxy orthosilicate (TEOS) or octamethyl cyclotetrasiloxane (OMTS) to a furnace after carbon black formation commenced as noted in Table 6 below. Furnace conditions were set so as to form products having similar surface areas and structure levels and, hence, pigmentary characteristics as the N-234-type carbon blacks. The amount of silicon in the carbon black, the DBP, the surface areas and the tint strengths of the silicon-containing carbon blacks formed are listed in Table 6 below.

TABLE 6

Characteristics Of the Silicon-Containing Carbon Blacks Formed By Addition of a Volatile Silicon Compound to the Furnace After Carbon Black Formation Commences

| Example | Silicon Compound | Weight % Silicon | DBP cc/100 g | $N_2$ Area $m^2/g$ | Tint Strength |
|---|---|---|---|---|---|
| 8 | OMTS | 2.2 | 115 | 140 | 118 |
| 9 | TEOS | 2.3 | 131 | 127 | 109 |
| 10 | TEOS | 4.2 | 122 | 115 | 103 |
| 11 | TEOS | 6.6 | 131 | 117 | 92 |

EXAMPLE 12

Attachment of p-$C_6H_4SO_3^-$ Groups to Silicon-Containing Carbon Blacks

A diazonium salt solution was prepared by adding sulfanilic acid (1.14 parts), 70% nitric acid (0.784 parts), and sodium nitrite (0.47 parts) to 100 parts deionized water at ambient temperatures. Immediately thereafter, 15 parts of a silicon-containing carbon black prepared according to the method of Example 7 were added, with stirring, to the diazonium salt solution. After stirring for one hour, the slurry was dried overnight at 85° C. to yield modified silicon-containing carbon black.

EXAMPLE 13

Attachment of p-$C_6H_4SO_3^-$ Groups to Silicon-Containing Carbon Blacks

A diazonium salt solution was prepared by adding sulfanilic acid (0.554 parts), 70% nitric acid (0.403 parts), and sodium nitrite (0.221 parts), to 50 parts deionized water chilled in an ice bath. Immediately thereafter, the diazonium salt solution was added to a slurry containing 75 parts deionized water and 6 parts of a silicon-containing carbon black prepared according to the method of Example 5. The resulting slurry was stirred for 30 minutes and then was dried overnight at 70° C. to yield modified silicon-containing carbon black.

EXAMPLE 14

Attachment of p-$C_6H_4SO_3^-$ Groups to Silicon-Containing Carbon Black

A diazonium salt solution was prepared by adding sulfanilic acid (0.924 parts), 70% nitric acid (0.672 parts), and sodium nitrite (0.368 parts) to 50 parts deionized water chilled in an ice bath. Immediately thereafter, the diazonium salt solution was added to a slurry containing 75 parts deionized water and 10 parts of a silicon-containing carbon black prepared according to the method of Example 10. The resulting slurry was stirred for 30 minutes and then was dried overnight at 70° C. to yield modified silicon-containing carbon black.

While the products of Examples 12–14 were not pelletized, the dried cakes had densities which were comparable with those of the pelletized silicon-containing carbon blacks and had better handling properties than their fluffy counterparts. Pelletized products could have been produced by adding the diazonium salt solution in the requisite volume of water required for converting the fluffy forms of the silicon-containing carbon blacks to pellets in a pin pelletizer.

EXAMPLE 15

Attachment of p-$C_6H_4CO_2^-$ Groups to the Surfaces of Silicon-Containing Carbon Black Stock solution A (19 parts of concentrated hydrochloric acid (about 36% HCl) and 20 parts water), and stock solution B (8.0 parts $NaNO_2$ and 39.2 parts water) were prepared. The stock solutions were chilled to 5° C.

1.58 g of anthranilic acid (o-amino benzoic acid) was added to 10.3 g of stock solution A. 10.5 g of stock solution B were then slowly added while ensuring that the temperature did not exceed 10° C. The resulting solution, kept in an ice bath, was stirred for 15 minutes and then was added to a slurry of 20 parts of a silicon-containing carbon black prepared according to the method of Example 5 dispersed in 300 parts water. The resulting slurry was stirred for 15 minutes and then was dried in an oven at 70° C. to yield modified silicon-containing carbon black.

EXAMPLE 16

Attachment of p-$C_6H_4CO_2^-$ Groups to the Surface of Silicon-Containing Carbon Black The method of Example 15 was followed, substituting a silicon-containing carbon black prepared according to the method of Example 10 for the silicon-containing carbon black.

The dried cakes of the modified silicon-containing carbon blacks of Examples 15 and 16 had densities which were comparable to those of pelletized products and had better handling properties than their fluffy precursors.

EXAMPLES 17–23

Dispersibility

The dispersibilities of pelletized modified silicon-containing carbon blacks (Examples 5 and 7) and pelletized modified silicon-containing carbon blacks having p-$C_6H_4SO_3^-$ groups (Examples 12–14) and p-$C_6H_4CO_2^-$ groups (Examples 15 and 16) attached to their surfaces were determined using the optical density procedure described above. Sonified slurry optical densities and percent changes in optical density are summarized in Table 7 below.

COMPARATIVE EXAMPLE 17A

Dispersibility

The dispersibility of carbon black prepared according to ASTM N-234 was determined according to the optical density procedure described above.

Results are summarized in Table 7 below.

TABLE 7

Change in Slurry Optical Densities on Sonification

| Example | (Carbon Black) | $(OD)_{sonified}$ | $\Delta(OD)$, % |
|---|---|---|---|
| 17A | (N-234) | 1.179 | 98.6 |
| 17 | (5) | 1.028 | 97.6 |
| 18 | (7) | 0.699 | 98.9 |
| 19 | (12) | 0.926 | 52.9 |
| 20 | (13) | 1.051 | 26.6 |
| 21 | (14) | 0.792 | 0.0 |
| 22 | (15) | 0.940 | 57.2 |
| 23 | (16) | 0.995 | 62.1 |

The $\Delta(OD)$ values of the pelletized ASTM N-234 carbon black used in Comparative Example 17A, and the silicon-containing blacks (Examples 17 and 18 and Comparative Example 17A) were close to 100%. This indicates that little dispersion took place under low shear stirring. The $\Delta(OD)$ values of the samples containing ionizable group attached to their surfaces were much smaller, ranging from 0 to 62%. This demonstrates that attachment of ionizable groups to the surfaces of the silicon-containing carbon blacks enhances their dispersibilities.

EXAMPLE 24

Colored Concrete Formulation with Red Iron Oxide and Silicon-Containing Carbon Black A pigment mixture was prepared by thoroughly mixing 90 parts of red iron oxide and 6.2 parts of a silicon-containing carbon black in a pestle and mortar until additional mixing gave no further color change. 1.4 parts of the pigment mixture was then mixed by spatula with 60 parts of sand and 14 parts of cement. About 10 parts of water were added, and the mixture was worked by spatula to form a paste. The paste was cast into channels (8.5 cm long×1 cm wide×1.5 cm deep) to prepare concrete forms which were allowed to dry slowly under ambient conditions. The reflectance spectra of the dry, colored concrete forms were determined, and the reflective values were used to compute L*, a*, and b* values.

COMPARATIVE EXAMPLE 24A

Colored Concrete Formulation with Red Iron Oxide and Carbon Blacks

Concrete forms were prepared according to the method of Example 24, substituting carbon black prepared according to ASTM N-234 for the silicon-containing carbon black. The reflectance spectra of the dry, colored concrete forms were determined, and the reflectance values were used to compute the International Commission on Illumination CIE 1976 L*, a*, and b* values.

COMPARATIVE EXAMPLES 24B–24D

Colored Concrete Formulation With Red Iron Oxide and Synthetic Black Iron Oxide Three sets of concrete forms were prepared according to the method of Example 24, substituting 18.6 parts, 31 parts, and 43.4 parts of synthetic black iron oxide for the silicon-containing carbon black, respectively. The reflectance spectra of the dry, colored concrete forms were determined, and the reflectance values were used to compute the International Commission on Illumination CIE 1976 L*, a*, and b* values.

EXAMPLE 25

Colored Concrete Formulation with Red Iron Oxide and Modified Silicon-Containing Carbon Black 1.4 parts of red iron oxide were mixed by spatula with 60 parts of sand and 14 parts of cement. 0.0875 part of a modified silicon-containing carbon black was dispersed in 10 parts of water under low shear dispersion conditions for 30 minutes using a magnetic stirrer. The aqueous modified silicon-containing carbon black was added to the sand/cement mixture to form a paste. The paste was cast into channels (8.5 cm long×1 cm wide×1.5 cm deep), to prepare concrete forms which were allowed to dry slowly under ambient conditions. The reflectance spectra of the dry, colored concrete forms were determined, and the reflective values were used to compute L*, a*, and b* values.

EXAMPLES 26–30

Colored Concrete Formulation with
Silicon-Containing Carbon Black

Concrete forms were prepared according to the method of Example 24, substituting the silicon-containing carbon blacks of Examples 3–7, respectively. The reflectance spectra of the dry, colored concrete were determined, and the reflectance values were used to compute International Commission On Illumination CIE 1976 L*, a*, and b*, values as described above.

The concrete forms were then weathered. The color values before acid washing and the change in color values after acid washing are listed in Table 8 below.

TABLE 8

Effects of Acid Washing Concrete Pigmented with
Silicon-Containing Carbon Black Formed by Addition
of a Volatile Silicon Compound to the Feedstock

| Example | L* | a* | b* | ΔL* | Δa* | Δb* |
|---|---|---|---|---|---|---|
| 26 | 47.29 | 4.50 | 7.61 | −5.66 | 0.31 | 1.66 |
| 27 | 49.09 | 4.92 | 7.57 | −5.34 | 0.19 | 1.52 |
| 28 | 45.24 | 4.93 | 7.96 | −6.71 | −0.25 | 0.40 |
| 29 | 48.05 | 4.49 | 7.51 | −6.91 | 0.07 | 1.52 |
| 30 | 50.01 | 5.46 | 9.33 | −6.04 | 0.19 | −0.27 |

COMPARATIVE EXAMPLES 26A–26C

Colored Concrete Formulation with Synthetic Black
Iron Oxide

Concrete forms prepared according to the methods of Example 24, substituting synthetic black iron oxide in amounts noted in Table 9 below. The reflectance spectra of the dry, colored concrete forms were determined and the reflectance values were used to compute the International Commission on Illumination CIE 1976 L*, a*, and b* values.

The concrete forms were then weathered. The color values before acid washing and the change in color values after acid washing are listed in Table 9 below.

TABLE 9

Effect of Acid Washing on the Color of Concrete
Pigmented with Synthetic Black Iron Oxide

| Comparative Example Number | ªPigment Amount | L* | a* | b* | ΔL* | Δa* | Δb* |
|---|---|---|---|---|---|---|---|
| 26A | 2.7 Times | 50.80 | 5.83 | 10.01 | −9.46 | 0.18 | 0.12 |
| 26B | 4.0 Times | 47.92 | 4.49 | 6.89 | −0.01 | −0.01 | 1.43 |
| 26C | 5.0 Times | 44.83 | 4.13 | 7.04 | −0.21 | −0.21 | 0.52 |

ªPigment amount represents the factor by which the synthetic black iron oxide content in the concrete is higher than that of carbon black based products.

The results in Table 9 show that as the amount of the synthetic black iron oxide in the concrete is increased, the L* value is reduced which corresponds to an increase in jetness (that is, darkness in color). The a* value also decreases, meaning the degree of redness is reduced, probably because the natural red iron oxide content of the concrete is reduced. Similarly, the degree of yellowness is decreased. On acid washing, the jetness increases as shown by the relatively large negative change in the value of ΔL*. On the other hand, the changes in the values of Δb* and, especially, Δa*, are quite small, demonstrating that the color shade of the concrete has not substantially changed with acid washing.

COMPARATIVE EXAMPLES 26D–26E

Colored Concrete Formulations with Carbon Black

Concrete forms were prepared according to the method of Example 24 substituting fluffy and pelletized carbon black prepared in accordance with ASTM N-234 as noted in Table 10 below for the pigment. The carbon black had a surface area of 123 m²/g, a pelletized DBP value of 122 cc/100 g carbon, and a tint strength of 122%. The reflectance spectra of the dry, colored concrete forms were determined and the reflectance values were used to compute the International Commission on Illumination CIE 1976 L*, a*, and b* values.

The concrete forms were then weathered. The color values before acid washing and the change in color values after acid washing are listed in Table 10 below.

TABLE 10

Effect of Acid Washing Concrete
Pigmented with a Conventional ASTM N-234 Carbon Black

| Comparative Example Number | Carbon Black State | L* | a* | b* | ΔL* | Δa* | Δb* |
|---|---|---|---|---|---|---|---|
| 26D | Fluffy | 47.74 | 4.98 | 6.96 | −5.40 | 0.69 | 3.30 |
| 26E | Pelletized | 49.74 | 4.89 | 6.57 | −7.01 | 1.09 | 3.35 |
| 26F | Pelletized | 45.46 | 4.59 | 5.78 | −3.91 | 0.37 | 3.34 |

Examples 26–30 in comparison with Comparative Examples 26D–26F illustrate that the color values attained using the silicon-containing carbon blacks are similar to those obtained with conventional carbon black. The L* values of the products tend to increase (i.e., become lighter) at the larger silicon contents in the products. This observation is in line with the tint strength values presented in Table 5. On acid washing, the ΔL* values are comparable with those for carbon black (Table 10). The magnitudes of the values of Δa* and Δb*, on the other hand, are smaller. This indicates that the change in color shade of the concrete pigmented with silicon-containing carbon black is less than that attained with conventional carbon black.

EXAMPLES 31–34

Colored Concrete Formulations with
Silicon-Containing Carbon Black

Concrete forms prepared according to the method of Example 24, substituting the silicon-containing carbon black of Examples 8–11, respectively. The reflectance spectra of the dry, colored concrete forms were determined and the reflectance values were used to compute International Commission on Illumination CIE 1976 L*, a*, and b* values as described above.

The concrete forms were then weathered. The color values before acid washing and the change in color values after acid washing are summarized in Table 11.

TABLE 11

Effects Of Acid Washing Concrete Pigmented With Silicon-Containing Carbon Black Formed By Addition of a Volatile Silicon Compound to the Furnace After Carbon Black Formation Commences

| Example | L* | a* | b* | ΔL* | Δa* | Δb* |
|---|---|---|---|---|---|---|
| 31 | 40.09 | 4.18 | 6.61 | −2.15 | 0.39 | 1.86 |
| 32 | 43.63 | 4.68 | 6.56 | −2.21 | 0.04 | 2.76 |
| 33 | 39.20 | 3.87 | 6.45 | −0.27 | 0.30 | 1.71 |
| 34 | 39.24 | 4.32 | 6.41 | +1.03 | 0.15 | 2.65 |

Examples 31–34 demonstrate that silicon-containing carbon blacks formed by addition of a volatile silicon compound after carbon black formation commences give concretes with somewhat jetter colors (reduced L* values) even at the higher silicon levels with the lower tint strengths than those formed with the blacks of Comparative Examples 26D–26F. This suggests that the silicon-containing carbon blacks used in the present invention are more compatible with the concrete than are conventional carbon blacks. Color shade, as given by the a* and b* values, are reasonably similar to those obtained with the carbon blacks of Comparative Examples 26D–26F. Changes in color on acid washing are relatively small and significantly smaller than those attained with the carbon blacks of Comparative Examples 26D–26F. This demonstrates that silicon-containing carbon black pigmented binder compositions are more resistant to weathering than are conventional carbon black pigmented binder compositions.

EXAMPLES 35–37

Colored Concrete Formulations with Modified Silicon-Containing Carbon Blacks

Concrete forms were prepared according to the method of Example 24, substituting the modified silicon-containing carbon blacks of Examples 12–14, respectively. The reflectance spectra of the dry, colored concrete were determined, and the reflectance values were used to compute International Commission on Illumination CIE 1976 L*, a*, and b* values as described above. The color values before acid washing and the change in color values after acid washing are summarized in Table 12 below.

TABLE 12

Effects Of Acid Washing Concrete Pigmented with Modified Silicon-Containing Carbon Blacks Having p-$C_6H_4SO^-$ Groups Attached to Their Surfaces

| Example | L* | a* | b* | ΔL* | Δa* | Δb* |
|---|---|---|---|---|---|---|
| 35 | 44.47 | 4.69 | 8.25 | −6.20 | −0.08 | 0.82 |
| 36 | 43.61 | 4.16 | 8.08 | −0.39 | −0.39 | −0.19 |
| 37 | 45.37 | 4.74 | 9.20 | −6.38 | −0.24 | −0.83 |

Comparison of Examples 35–37 with Comparative Examples 26A–26C (synthetic black iron oxide) having similar jetness values indicates that the change in color on acid washing, as shown by the magnitudes of Δa* and Δb*, of the two sets of pigments are small and reasonably comparable. This demonstrates that the weathering properties of modified silicon-containing carbon blacks having p-$C_6H_4SO_3^-$ groups attached to their surfaces are better than those of conventional blacks and somewhat better than those of the unmodified silicon-containing carbon blacks.

EXAMPLES 38 AND 39

Colored Concrete Formulations with Modified Silicon-Containing Carbon Blacks

Concrete forms were prepared according to the method of Example 24, substituting the modified silicon-containing carbon blacks of Examples 15 and 16, respectively. The reflectance spectra of the dry, colored concrete were determined, and the reflectance values were used to compute International Commission on Illumination CIE 1976 L*, a*, and b* values as described above.

The concrete forms were weathered. The color values before acid washing and the change in color values after acid washing are summarized in Table 13 below.

TABLE 13

Effects Of Acid Washing Concrete Pigmented with Silicon-Containing Carbon Blacks Having p-$C_6H_4CO_2^-$ Groups Attached to Their Surfaces

| Example | L* | a* | b* | ΔL* | Δa* | Δb* |
|---|---|---|---|---|---|---|
| 38 | 47.02 | 4.75 | 8.55 | −5.70 | −0.02 | 0.70 |
| 39 | 45.14 | 4.09 | 7.53 | −4.49 | −0.20 | 0.60 |

Comparison of Examples 38 and 39 with Comparative Examples 26A–26C (synthetic black iron oxide) having similar jetness values indicates that the changes in color on acid washing of the two sets of pigments are small and reasonably comparable. This demonstrates that the weathering properties of the modified silicon-containing blacks having p-$C_6H_4CO_2^-$ groups attached to their surfaces are better than those of conventional blacks and somewhat better than those of the unmodified silicon-containing carbon blacks.

EXAMPLES 40–44

Colored Concrete Formulations with Modified Silicon-Containing Carbon Blacks

Concrete forms were prepared according to the method of Example 24, substituting the modified silicon-containing carbon blacks of Examples 12–16, respectively, for the silicon-containing carbon black. However, the modified silicon-containing carbon black product (0.0875 parts) was added to the water used to set the concrete. None was added to the natural red iron oxide. The treated silicon-containing black was dispersed in the water under low shear dispersion conditions by stirring for 30 minutes using a magnetic stirrer. The reflectance spectra of the dry, colored concrete were determined, and the reflectance values were used to compute International Commission on Illumination CIE 1976 L*, a*, and b* values as described above.

The concrete forms were weathered. The color values before acid washing and the change in color values after acid washing are summarized in Table 14.

TABLE 14

Effect of Coloring Concrete Using Procedure II with Silicon-Containing Carbon Blacks Having p-C$_6$H$_4$SO$_3^-$ and p-C$_6$H$_4$CO$_2^-$ Groups Attached to Their Surfaces

| Example | L* | a* | b* | ΔL* | Δa* | Δb* |
|---|---|---|---|---|---|---|
| 40 | 45.73 | 3.79 | 7.59 | −4.95 | −0.17 | 0.64 |
| 41 | 42.55 | 3.40 | 7.08 | −4.21 | −0.26 | 0.14 |
| 42 | 48.15 | 4.16 | 8.22 | −7.38 | −0.28 | −0.30 |
| 43 | 48.85 | 4.70 | 8.54 | −5.82 | 0.15 | −0.05 |
| 44 | 49.54 | 4.42 | 8.62 | −6.30 | 0.09 | 0.20 |

The L*, a*, and b* values of each of Examples 40–44 are similar to those of Examples 35–39. This demonstrates that the modified silicon-containing carbon blacks having attached organic groups containing an ionic or an ionizable group are readily dispersed using low shear dispersion conditions. Moreover, the changes in color resulting from acid washing are also similar and small for the Δa* and Δb* values which demonstrates their enhanced weathering properties.

All patents, applications, test methods, and publications mentioned herein are hereby incorporated by references.

Many variations of the present invention will suggest themselves to those skilled in the art in light of the above detailed disclosure. All such modifications are within the full intended scope of the appended claims.

We claim:

1. A binder composition comprising
    (a) a mineral binder, and
    (b) a silicon-containing carbon black.

2. A binder composition as defined in claim 1, wherein said mineral binder is cement, concrete, mortar, or exterior plaster.

3. A binder composition as defined in claim 1, wherein said silicon-containing carbon black is oxidized.

4. A binder composition as defined in claim 3, wherein said silicon-containing carbon black is oxidized by nitric acid.

5. A binder composition as defined in claim 1, wherein said silicon-containing carbon black has attached an organic group containing an ionic or ionizable group.

6. A binder composition as defined in claim 5, wherein said ionic or ionizable group is a carboxylic acid or a salt thereof, a sulfonic acid or a salt thereof, a sulfophenyl group or a salt thereof, a carboxyphenyl group or a salt thereof, or any combination thereof.

7. A binder composition as defined in claim 1, wherein said silicon-containing carbon black is pelletized.

8. A binder composition as defined in claim 5, wherein said silicon-containing carbon black is water dispersible.

9. A binder composition as defined in claim 1, wherein said silicon-containing carbon black is dispersed by a low shear method.

10. A binder composition as defined in claim 1, wherein said silicon-containing carbon black comprises from about 0.1 to about 20 parts by weight of silicon, based upon 100 parts by weight of silicon-containing carbon black.

11. A binder composition as defined in claim 10, wherein said silicon-containing carbon black comprises from about 1 to about 10 parts by weight of silicon, based upon 100 parts by weight of silicon-containing carbon black.

12. A binder composition as defined in claim 1 comprising about 5 or less parts by weight of silicon-containing carbon black, based upon 100 parts by weight of total composition.

13. A binder composition as defined in claim 12, comprising from about 0.1 to about 1 part by weight of silicon-containing carbon black based upon 100 parts by weight of total composition.

14. A binder composition as defined in claim 1, wherein said silicon-containing carbon black has silicon-containing regions at the surface of said carbon black.

15. A binder composition as defined in claim 1, wherein said silicon-containing carbon black comprises a carbon black aggregate wherein silicon-containing regions are distributed throughout at least a portion of said aggregate and wherein at least a portion of said silicon-containing regions are accessible to the surface of said aggregate.

16. A binder composition as defined in claim 1, wherein said silicon-containing carbon black is prepared by interaction between incomplete combustion products of a hydrocarbon and decomposition products of a volatilizable silicon-containing compound in a furnace reactor.

17. A binder composition as defined in claim 15, wherein said volatilizable compound is octamethyl-cyclotetrasiloxane, tetraethoxy silane, tetramethoxy orthosilicate, tetrachlorosilane, trichloromethylsilane, or mixtures thereof.

18. A binder composition as defined in claim 15, wherein said silicon-containing carbon black is oxidized.

19. A binder composition as defined in claim 18, wherein said silicon-containing carbon black is oxidized by nitric acid.

20. A binder composition as defined in claim 15, wherein said silicon-containing carbon black has attached an organic group containing an ionic or an ionizable group.

21. A binder composition as defined in claim 20, wherein said ionic or ionizable group is a carboxylic acid or a salt thereof, a sulfonic acid or a salt thereof, a sulfophenyl group or a salt thereof, a carboxyphenyl group or a salt thereof, or any combination thereof.

22. A binder composition as defined in claim 15, wherein said silicon-containing carbon black is pelletized.

23. A binder composition as defined in claim 20, wherein said silicon-containing carbon black is water dispersible.

24. A binder composition as defined in claim 20, wherein said silicon-containing carbon black is dispersed by a low shear method.

25. A binder composition as defined in claim 15, wherein said mineral binder is cement, concrete, mortar, or exterior plaster.

26. A binder composition as defined in claim 15, wherein said silicon-containing carbon black comprises from about 0.1 to about 20 parts by weight of silicon based upon 100 parts by weight of silicon-containing carbon black.

27. A binder composition as defined in claim 26, wherein said silicon-containing carbon black comprises from about 1 to about 10 parts by weight of silicon based upon 100 parts by weight of silicon-containing carbon black.

28. A binder composition as defined in claim 15, comprising about 5 or less parts by weight of silicon-containing carbon black, based upon 100 parts by weight of total composition.

29. A binder composition as defined in claim 29, comprising from about 0.1 to about 1 part by weight of silicon-containing carbon black based upon 100 parts by weight of total composition.

30. The binder composition of claim 1, further comprising iron oxide, silica, carbon black, carbon black having an attached organic group containing an ionic or ionizable group, or combinations thereof.

31. The binder composition of claim 5, further comprising iron oxide, silica, carbon black, or combinations thereof.

32. A method for improving the color stability of a mineral binder composition, said method comprising adding to said mineral binder a silicon-containing carbon black.

33. A method as defined in claim 32, wherein said silicon-containing carbon black has attached an organic group containing an ionic or an ionizable group.

34. An article formed from a binder composition comprising:
(a) a mineral binder, and
(b) a silicon-containing carbon black.

35. An article as defined in claim 34, wherein said article is a roofing tile.

36. A binder composition comprising:
(a) a mineral binder; and
(b) a carbon black aggregate comprising a region of at least one silicon-containing specie located intrinsically at the surface of or within the carbon black aggregate.

37. The binder composition of claim 36, wherein said carbon black aggregate has a greater nitrogen surface area after extraction with hydrofluoric acid compared to carbon black not having any regions of silicon-containing species.

38. The binder composition of claim 37, wherein said carbon black aggregate has a nitrogen surface area that is at least 4 $m^2/g$ more than carbon black not having any regions of silicon-containing species.

* * * * *